(12) United States Patent
Ghalebi et al.

(10) Patent No.: US 12,247,758 B2
(45) Date of Patent: Mar. 11, 2025

(54) REPLACEABLE UV LAMP CARTRIDGE FOR AIR PURIFICATION SYSTEMS

(71) Applicant: Air Purix Inc., Delray Beach, FL (US)

(72) Inventors: Mehrdad Ghalebi, Delray Beach, FL (US); Robert L. Diamond, Palm Beach, FL (US)

(73) Assignee: Air Purix Inc., Delray Beach, FL (US)

( * ) Notice: Subject to any disclaimer, the term of this patent is extended or adjusted under 35 U.S.C. 154(b) by 529 days.

(21) Appl. No.: 17/694,127

(22) Filed: Mar. 14, 2022

(65) Prior Publication Data

US 2022/0288267 A1 Sep. 15, 2022

Related U.S. Application Data

(60) Provisional application No. 63/286,338, filed on Dec. 6, 2021, provisional application No. 63/160,161, filed on Mar. 12, 2021.

(51) Int. Cl.

| F24F 13/28 | (2006.01) |
|---|---|
| A61L 9/20 | (2006.01) |
| B01D 46/00 | (2022.01) |
| B01D 46/24 | (2006.01) |
| B01D 46/681 | (2022.01) |
| B01D 46/78 | (2022.01) |

(52) U.S. Cl.
CPC ............ *F24F 13/28* (2013.01); *A61L 9/20* (2013.01); *A61L 9/205* (2013.01); *B01D 46/0028* (2013.01); *B01D 46/2411* (2013.01); *B01D 46/681* (2022.01); *B01D 46/78* (2022.01); *A61L 2209/11* (2013.01); *A61L 2209/12* (2013.01); *A61L 2209/133* (2013.01); *A61L 2209/14* (2013.01); *A61L 2209/212* (2013.01); *B01D 2279/40* (2013.01); *B01D 2279/65* (2013.01)

(58) Field of Classification Search
CPC ..... F24F 8/22; F24F 13/28; A61L 9/20; A61L 9/205; A61L 2209/133; B01D 46/0028
See application file for complete search history.

(56) References Cited

U.S. PATENT DOCUMENTS

| 1,375,378 A | 4/1921 | Gaddess |  |
|---|---|---|---|
| 3,786,391 A * | 1/1974 | Mathauser | ......... H01R 13/6205 439/246 |
| 5,505,904 A | 4/1996 | Haidinger |  |
| 2003/0001113 A1* | 1/2003 | Witham | .................... A61L 9/20 250/504 R |

(Continued)

FOREIGN PATENT DOCUMENTS

KR 101419860 B1 * 7/2014

OTHER PUBLICATIONS

U.S. Appl. No. 17/692,713, filed Mar. 11, 2022.
U.S. NonFinal Office Action for U.S. Appl. No. 17/692,713, mailed on Nov. 22, 2024.

*Primary Examiner* — Robert Clemente
(74) *Attorney, Agent, or Firm* — Lowenstein Sandler LLP

(57) ABSTRACT

An example replaceable ultraviolet (UV) lamp cartridge includes: a tamper-proof UV energy absorbing shell containing one or more UV radiation emitting devices; an air inlet disposed at a first end of the tamper-proof UV energy absorbing shell; an air outlet disposed at a second end of the tamper-proof UV energy absorbing shell; and a self-aligning connector for receiving external voltage to be supplied to the UV energy emitting devices.

20 Claims, 8 Drawing Sheets

(56) References Cited

U.S. PATENT DOCUMENTS

| | | | |
|---|---|---|---|
| 2006/0049368 A1* | 3/2006 | Culbert | A61L 9/20 |
| | | | 250/503.1 |
| 2021/0283297 A1 | 9/2021 | Kim | |
| 2022/0018558 A1* | 1/2022 | Blaiotta | F24F 13/14 |
| 2022/0290892 A1* | 9/2022 | Ghalebi | F24F 8/22 |
| 2024/0316239 A1* | 9/2024 | Tripodi | A61M 16/10 |

* cited by examiner

REPLACEABLE UV LAMP CARTRIDGE FOR AIR PURIFICATION SYSTEMS

REFERENCE TO RELATED APPLICATION

This application claims the benefit of U.S. Provisional Patent Application No. 63/160,161, filed Mar. 12, 2021 and U.S. Provisional Patent Application No. 63/286,338, filed Dec. 6, 2021. The above-referenced applications are incorporated herein by reference.

TECHNICAL FIELD

The present disclosure is generally related to air purification systems, and is specifically related to replaceable ultraviolet (UV) cartridges for air purification systems and apparatuses.

BACKGROUND

"UV radiation" herein refers to electromagnetic radiation corresponding to the electromagnetic spectrum between the X-rays and visible light. UV radiation may include multiple types of UV rays, including UVA, UVB, and UVC, which differ by their respective wavelength: UVA rays have the longest wavelengths, followed by UVB, and UVC rays which have the shortest wavelengths. Thus, UVC radiation is the highest energy portion of the UV radiation spectrum.

BRIEF DESCRIPTION OF THE DRAWINGS

The present disclosure is illustrated by way of examples, and not by way of limitation, and may be more fully understood with references to the following detailed description when considered in connection with the figures, in which.

DETAILED DESCRIPTION

Figure 1A:
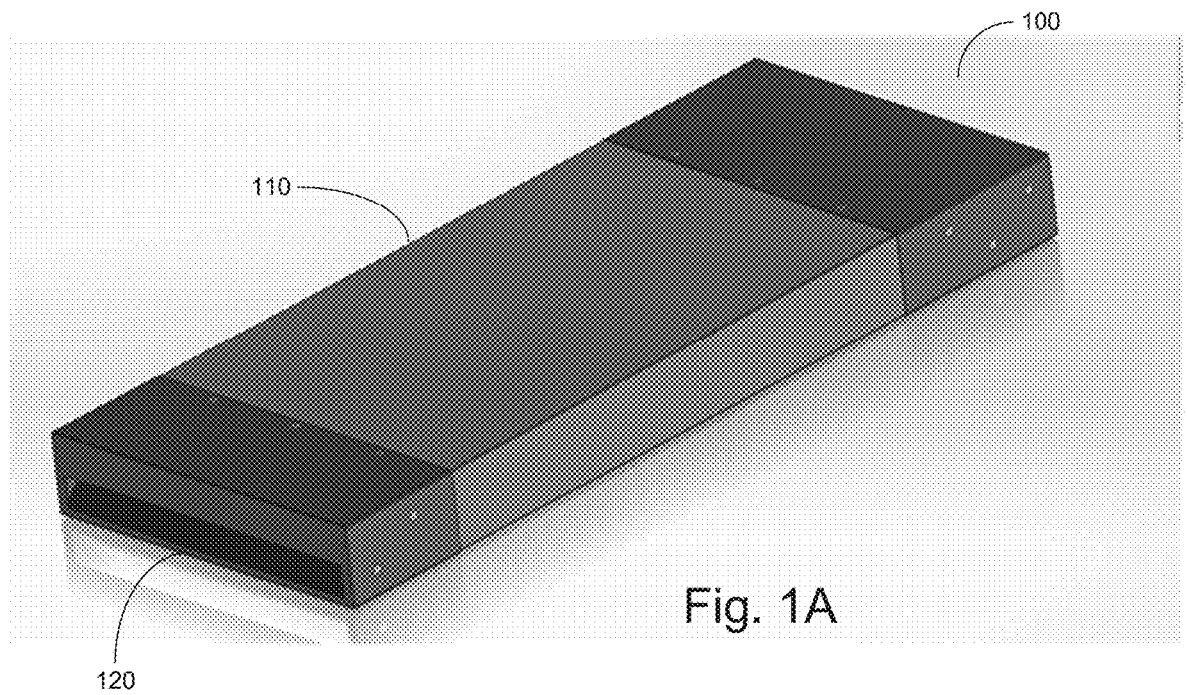
FIGS. 1A-1B show top oblique views of an example UV lamp cartridge implemented in accordance with aspects of the present disclosure.

Described herein are air purification systems, apparatuses, and devices employing particle filters and ultraviolet (UV) radiation emitters. Further described herein are replaceable UV lamp cartridges for such air purification systems, apparatuses, and devices.

An example air purification system, apparatus, or device (referred to as "air purification system" herein) may include a housing containing one or more air trims, one or more particle absorbing filters, one or more fans that force the air through the air trims and particle absorbing filters, and one or more UV radiation emitting devices. The shapes and locations of the air trims may be designed to control the direction of air moving through the air purification system. The particle absorbing filters may be represented, e.g., by high-efficiency particulate absorbing (HEPA) particle absorbing filters.

In operation, the airflow is inhaled into the housing through the inlet and is driven by the fan along the air path controlled by the air trims through the filters and around the UV emitting devices, until the airflow leaves the housing through the outlet. The filters retain the particles contained by the air, while the UV radiation effectively eliminates or deactivates a wide range of pathogenic microorganisms, such as bacteria and viruses, thus providing the requisite level of air purification.

Some amount of the UV radiation emitted by the UV radiation emitting devices would inevitably leak from the housing, e.g., through the air path outlet. The maximum amount of UV radiation that may be emitted by the air purification system may be regulated by various rules and standards. For example, UL507 specifies that the intensity of UVC radiation emitted by a device to the outside world should not exceed 0.1 $\mu W/cm^2$. Accordingly, the housing of the air purification system should effectively attenuate the UV energy (and, specifically, UVC energy, which is the highest energy potion of the UV radiation spectrum) in order to reduce the UV (and, specifically, UVC) leakage to values below the allowed maximum, while not obstructing the flow of air through the air filters and around the UV radiation emitting devices.

Furthermore, while UV radiation emitting devices utilized by air purification systems may have a limited useful life, pertinent rules and standards do not allow the end user to replace the UV radiation emitting devices. Accordingly, in order to protect the end user from potentially dangerous exposure to UV radiation, the air purification system may be equipped with a safety switch that would cut off the power supply to the UV emitting devices once any lids or doors in the housing are opened and/or once an attempt to physically tamper with the housing integrity is detected.

In order to satisfy the above-referenced and other design requirements, in some embodiments, the UV radiation emitting devices may be placed into a tamper-proof replaceable module ("UV lamp cartridge"), which the end user may remove at the end of the useful life of the UV radiation emitting devices. The end user may replace the removed UV lamp cartridge with a new one, while the old UV lamp cartridge may be shipped to a manufacturing facility for refurbishing. Thus, the replaceable UV lamp cartridge implemented in accordance with aspects of the present disclosure guarantees compliance with rules and standards regulating both maximum UV radiation leakage and end user safety, since removal of the UV lamp cartridge from the housing would necessarily cut off the power to the UV radiation emitting devices.

Figure 1B:
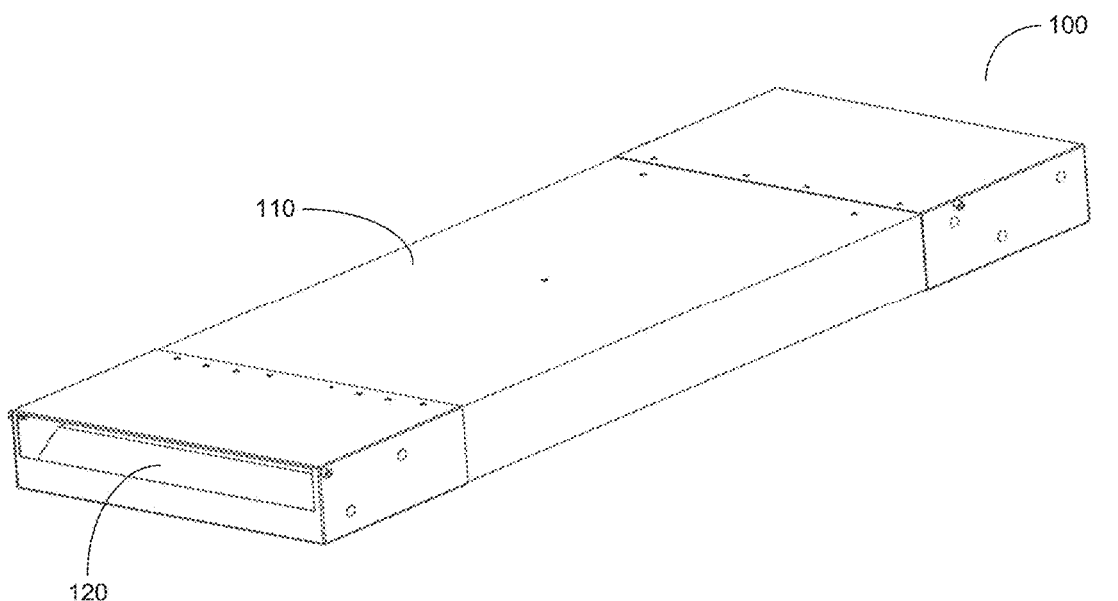
Figure 1C:
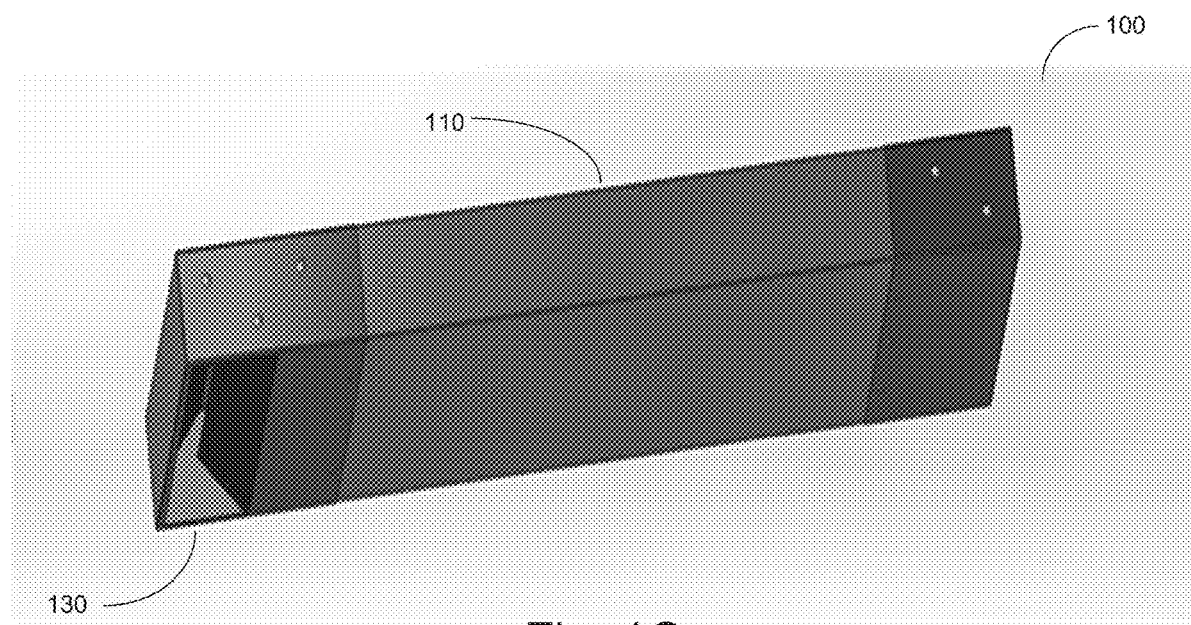
FIGS. 1C-1D shows the bottom oblique view of the example UV lamp cartridge implemented in accordance with aspects of the present disclosure.
Figure 1D:
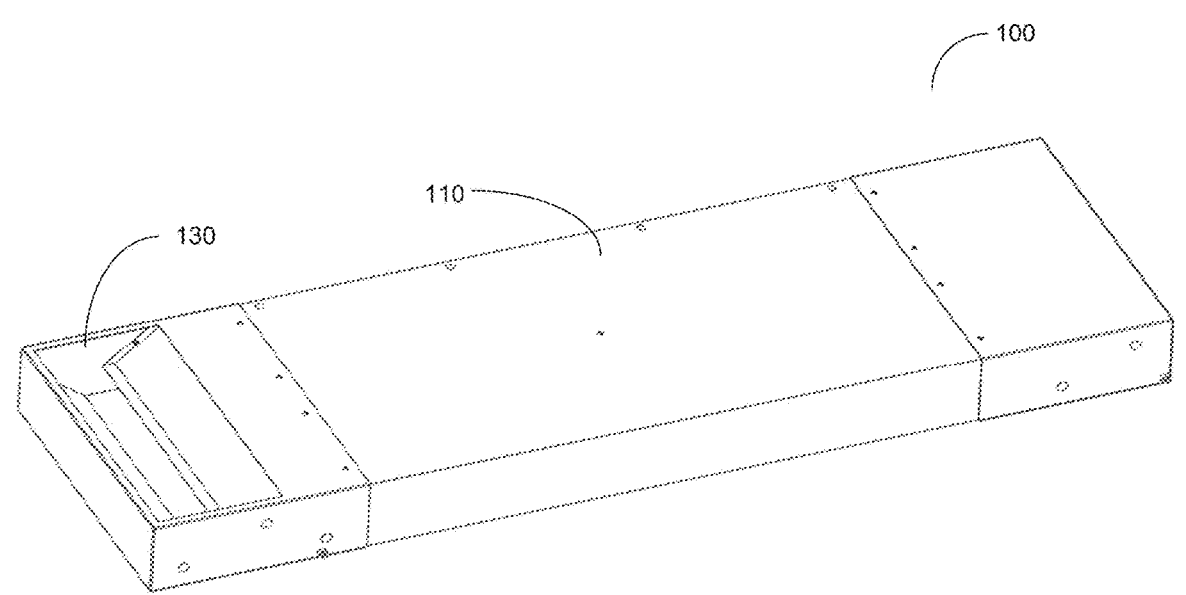

FIGS. 1A-1D show oblique views of an example UV lamp cartridge implemented in accordance with aspects of the present disclosure. In particular, FIGS. 1A-1B show top oblique views and FIGS. 1C-1D shows the bottom oblique view of the example UV lamp cartridge 100.

As shown in FIGS. 1A-1D, an example UV lamp cartridge 100 may include a tamper-proof UV energy absorbing shell 110 containing one or more UV radiation emitting devices (not shown in FIGS. 1A-1D). The UV energy absorbing shell is equipped with an air inlet 120 and an air outlet 130, such that the airflow would enter the UV energy absorbing shell 100 through the air inlet 120, and follow the air path controlled by optional air trims (e.g., inlet air trims 125A-125B and outlet air trims 135A-135C shown in FIGS. 2A-2B) around the UV emitting devices before leaving the UV energy absorbing shell 110 through the air outlet 130. As schematically illustrated by FIGS. 1A-1D, the air inlet 120 is a rectangular opening in a side (vertically oriented) facet, while the air outlet 130 is a rectangular opening in the bottom (horizontally oriented) facet and on the opposite, with respect to the air inlet 120, end of the imaginary longitudinal axis of the UV energy absorbing shell 110. Thus, there is a 90-degree angle between the side facet in which the air inlet 120 is located and the bottom facet in which the air outlet 130 is located. In various other implementations, other positions, orientations, and locations of the air inlet 120 and air outlet 130 may be utilized.

In various implementations, the above-referenced and/or other parts of the UV lamp cartridge 100 may be made of metal, plastic, composite, and/or other suitable materials. Surfaces of the above-referenced parts may be machined, polished, coated, painted, and/or otherwise processed.

The UV lamp cartridge 100 may be factory sealed, such that all external panels of the UV lamp cartridge 100 may be attached to each other in an airtight manner that would thwart any attempt by the end user to disassemble the UV lamp cartridge. In an illustrative example, welding may be used for connecting together the external panels of UV lamp cartridge 100. In another illustrative example, the external panels of UV lamp cartridge 100 may be attached to each other by rivets and/or bolts having their respective heads flushed and/or polished thus preventing their removal and ensuring the tamper-proof features of the UV lamp cartridge 100.

In some implementations, the replaceable UV lamp cartridge 100 may be equipped with a self-aligning connector (not shown in FIGS. 1A-1D) to ensure the proper positioning of the UV lamp cartridge 100 within an air purification system housing and to make electrical contact once the module is placed in situ (e.g., inserted into the air purification system), in order to supply the outside voltage to the UV radiation emitting devices 150.

Figure 2A:
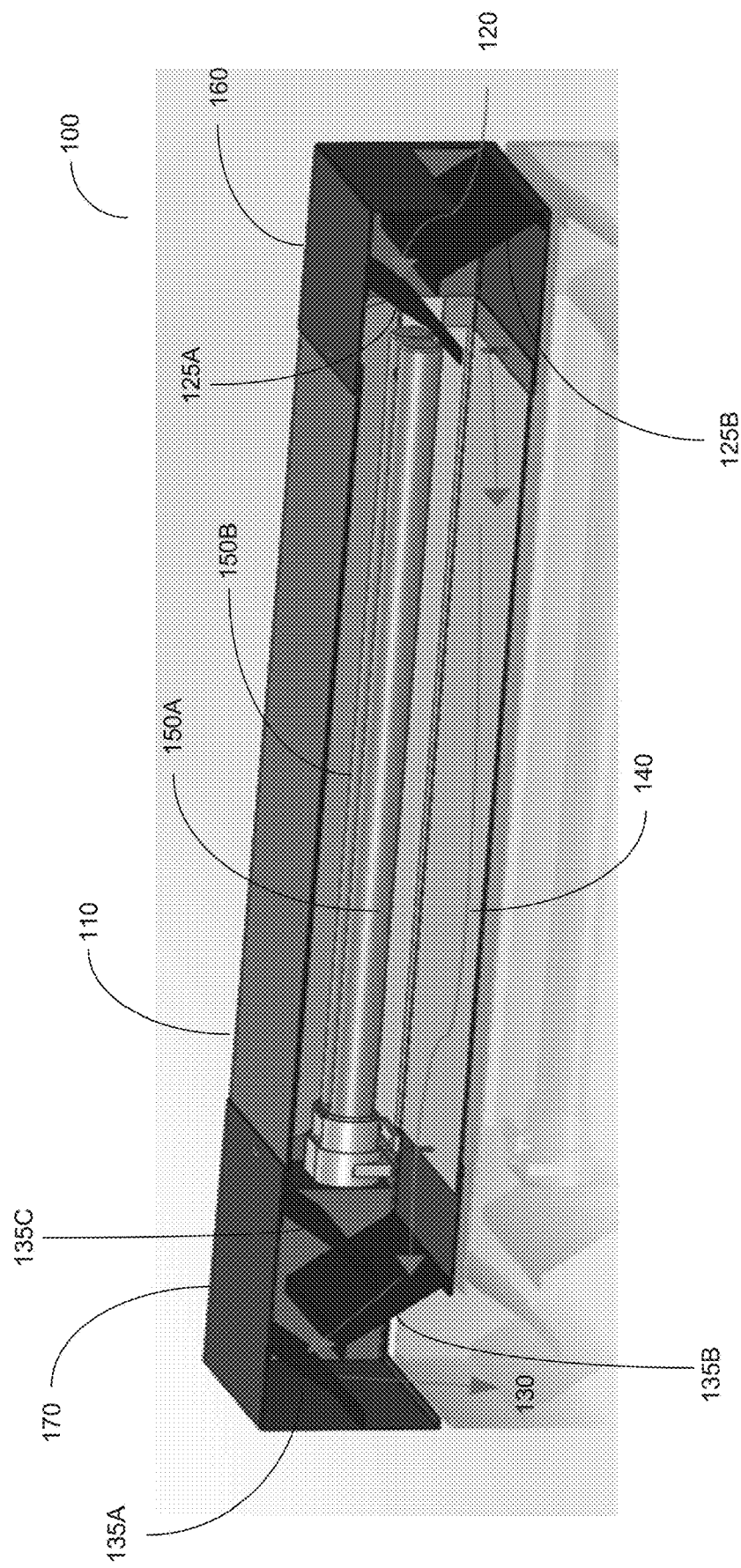
FIGS. 2A-2B show perspective cutaway views of the example UV lamp cartridge implemented in accordance with aspects of the present disclosure.
Figure 2B:
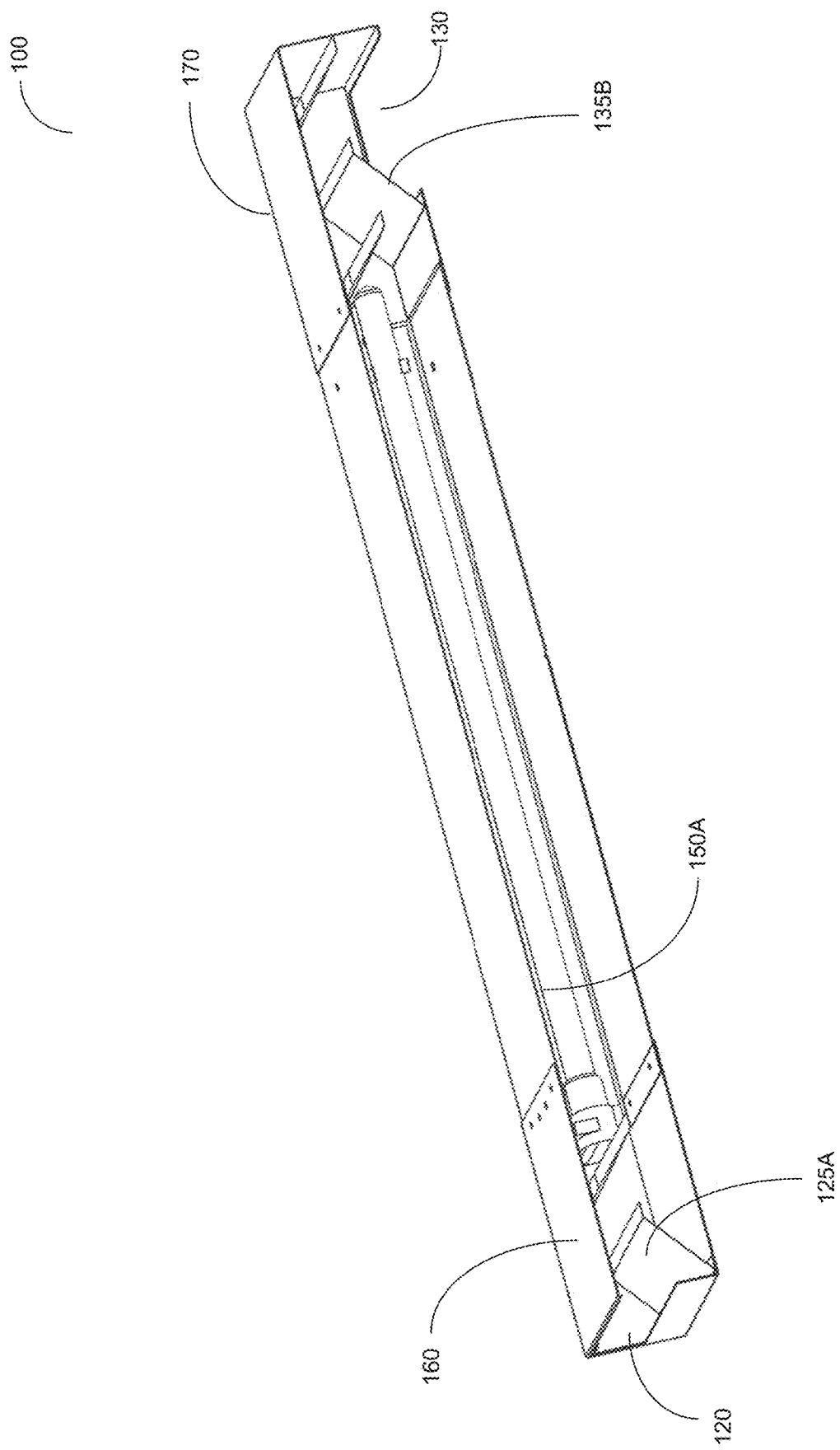

FIGS. 2A-2B show perspective cutaway views illustrating the air path through the UV lamp cartridge 100. As schematically illustrated by FIGS. 2A-2B, the above-described positioning of the air inlet 120 and the air outlet 130 forces the air to enter the UV lamp cartridge 100 via the air inlet 120 in the direction that is parallel to the imaginary longitudinal axis of the UV energy absorbing shell 110 and further forces the air to exit the UV lamp cartridge 100 via the air outlet 130 in the direction that is orthogonal to the imaginary longitudinal axis of the UV energy absorbing shell 110 (and therefore orthogonal to the direction in which the air enters the UV lamp cartridge 100). The air flow is directed by the inlet air trims 125A-125B and the outlet air trims 135A-135C.

The inlet air trims 125A-125B may be shaped and positioned to deflect the incoming air flow without changing its general direction, which is parallel to the imaginary longitudinal axis of the UV energy absorbing shell 110. Deflecting the incoming air flow by the inlet air trims 125A-125B would introduce some turbulence into it, thus increasing the exposure time of the air to the UV radiation emitted by the UV radiation emitting devices 150A-150K. Furthermore, the inlet air trims 125A-125B may also act as effective UV isolators, which impede an otherwise possible path to the outside world for UV radiation emitted by the UV radiation emitting devices 150, as described in more detail herein below.

The outlet air trims 135A-135B may be shaped and positioned to deflect and change the direction of the air flow before the air flow is discharged from the UV lamp cartridge 100. In the illustrative examples of FIGS. 2A-2B, the air, which enters the UV lamp cartridge 100 through the air inlet 120 in the direction which is parallel to the imaginary longitudinal axis of the UV energy absorbing shell 110, overflows the UV radiation emitting devices 150A-150K and is forced by the outlet air trims 135A-135C to leave the UV energy absorbing shell 110 in the direction which is perpendicular to the imaginary longitudinal axis of the UV energy absorbing shell 110. Furthermore, the outlet air trims 135A-135B may also act as effective UV isolators, which impede an otherwise possible path to the outside world for UV radiation emitted by the UV radiation emitting devices 150, as described in more detail herein below.

Thus, the air path 140 followed by the air driven through the UV lamp cartridge 100 overflows the UV radiation emitting devices 150A-150K, which are installed within the UV energy absorbing shell 110, thus ensuring that the UV radiation emitted by the UV radiation emitting devices 150 would effectively eliminate or deactivate a wide range of pathogenic microorganisms, such as bacteria and viruses, that may contained in the air.

In various implementations, the UV radiation emitting devices 150 may be represented, e.g., by light emitting diode (LED) lamps, low-pressure mercury-vapor lamps, amalgam lamps, high-intensity discharge (HID) lamps, plasma lamps, etc., which emit UV radiation having wavelengths within a certain range, e.g., between 200 and 280 nm. The UV radiation emitting devices 150 may be powered by an external power supply via an optional UV ballast circuit, which may be employed for ramping up the input voltage and producing a requisite output voltage for driving the UV radiation emitting devices 150. While four UV radiation emitting devices 150A-150K are shown in FIG. 4, other implementations may include various other numbers of UV radiation emitting devices 150.

Figure 3A:
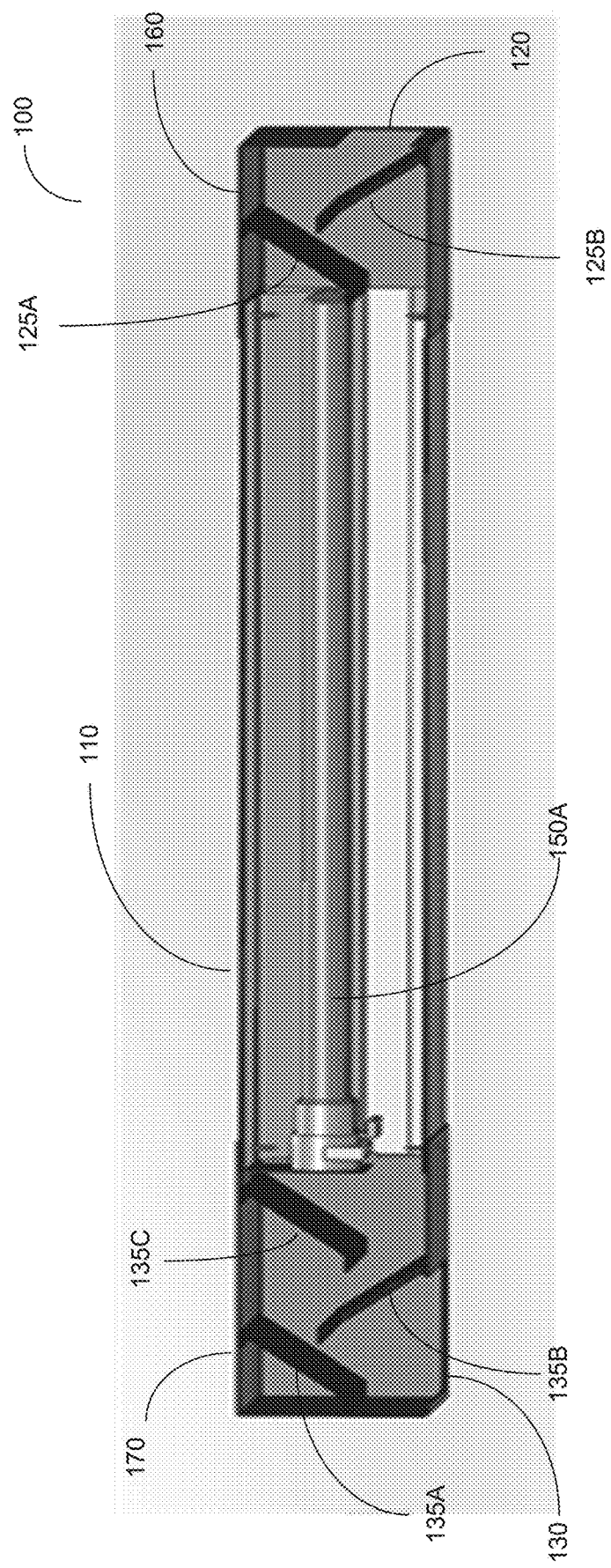
FIGS. 3A-3B show side cutaway views of the example UV lamp cartridge implemented in accordance with aspects of the present disclosure.
Figure 3B:
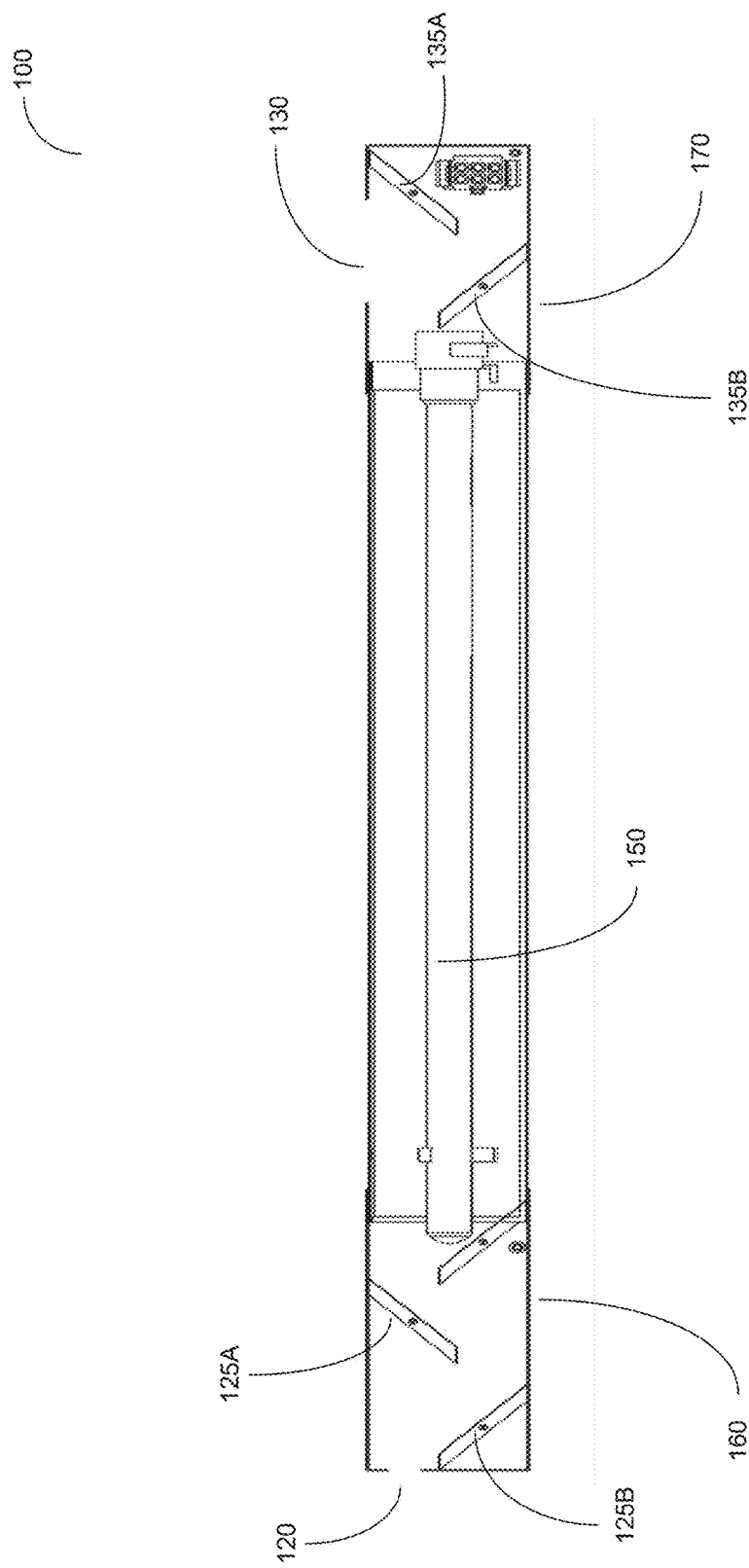

As schematically illustrated by FIGS. 3A-3B, which show side cutaway views of the UV lamp cartridge 100, the UV energy absorbing shell 110 may be formed by multiple flat panel facets that are arranged to form a convex polyhedron (e.g., a rectangular parallelepiped). The air inlet assembly 160 and air outlet assembly 170, which may be considered as extensions of the UV energy absorbing shell 110, may be attached to the respective ends of the UV energy absorbing shell 110 in an airtight manner.

The inner surfaces of the facets forming the UV energy absorbing shell 110 may be polished to provide a high reflectance (e.g., a reflectance value exceeding a predefined high reflectance threshold), thus collectively forming a light path to be followed by UV energy emitted by the UV radiation emitting devices 150. Conversely, the surfaces of the air trims 125, 135 and/or some other inner surfaces of the UV energy absorbing shell 110 may have a very low reflectance (e.g., a reflectance value falling below a predefined low reflectance threshold), such that each low reflective surface would absorb at least a predefined portion of UV energy (and, specifically UVC energy) incident upon the surface (e.g., 95% of the incident UV energy). Thus, the light path followed by the UV radiation emitted by the UV radiation emitting devices 150 may be constructed to include the requisite number of low reflectance surfaces in order to cause absorption of most of the UV radiation within the UV energy absorbing shell 110, in order to satisfy the pertinent rules and standards with respect to the amount of the UV energy (and, specifically UVC energy) that is allowed to be emitted by the air purification system.

Figure 4:
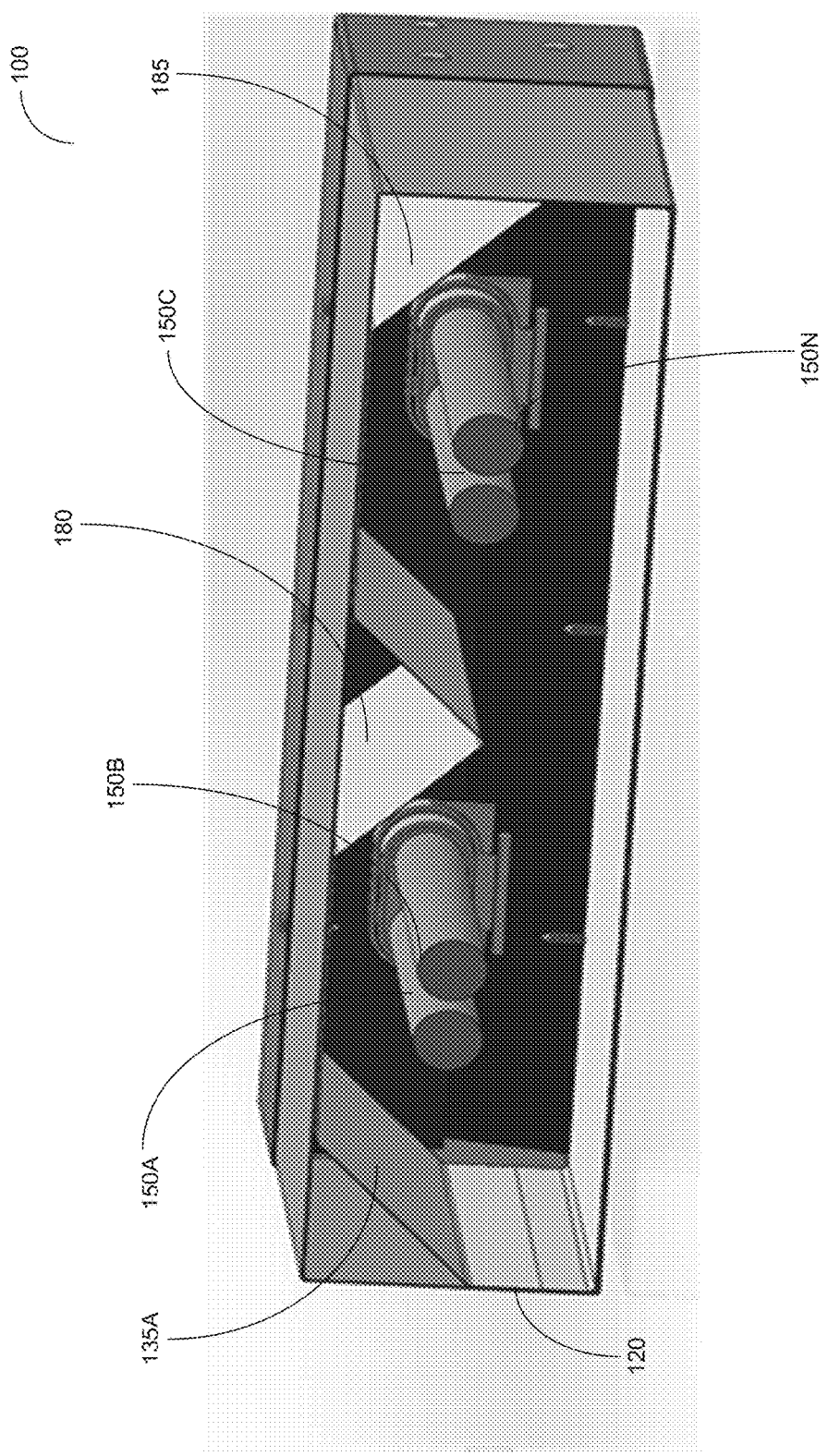
FIG. 4 shows a cross-section of the example UV lamp cartridge implemented in accordance with aspects of the present disclosure.

As schematically illustrated by FIG. 4, which shows a cross-section of the UV lamp cartridge 100, UV energy absorbing shell 110 may contain additional air trims 180, 185 having reflective surfaces. Similarly to the above-references air trims 125, 135, the air trims 180, 185 may be employed for directing the air flow within the UV energy absorbing shell 110 and/or reflecting the UV radiation emitted by the UV radiation emitting devices 150. In particular, the air trim 185 may be installed symmetrically, with respect to the imaginary longitudinal axis of the UV energy absorbing shell 110, to the outlet air trim 135A. The air trim 135 may be represented by a beam having a V-shaped cross-section, and may installed, parallel to the imaginary longitudinal axis of the UV energy absorbing shell 110, between two UV radiation emitting devices 150, thus introducing additional turbulence into the air flow, as well as providing additional reflective surfaces for the UV radiation emitted by the UV radiation emitting devices 150.

In some implementations, the UV lamp cartridge 100 may be equipped with an optional auxiliary fan, which may be installed within the UV energy absorbing shell 110 in order to facilitate the air movement through the UV energy absorbing shell 110.

In some implementations, the UV lamp cartridge 100 may be equipped with an optional particle absorbing filter, which may be installed at the inlet end of the UV lamp cartridge 100. The particle absorbing filter may be represented, e.g., by a high-efficiency particulate absorbing (HEPA) particle absorbing filter.

The above-described arrangement of the parts of the UV lamp cartridge 100 allows reducing the vertical size of the UV lamp cartridge, thus rendering the UV lamp cartridge 100 suitable for air purification systems installed in a wide range of environments, including elevator cabins, medical facilities, conference rooms, performance auditoriums, etc.

Figure 5:
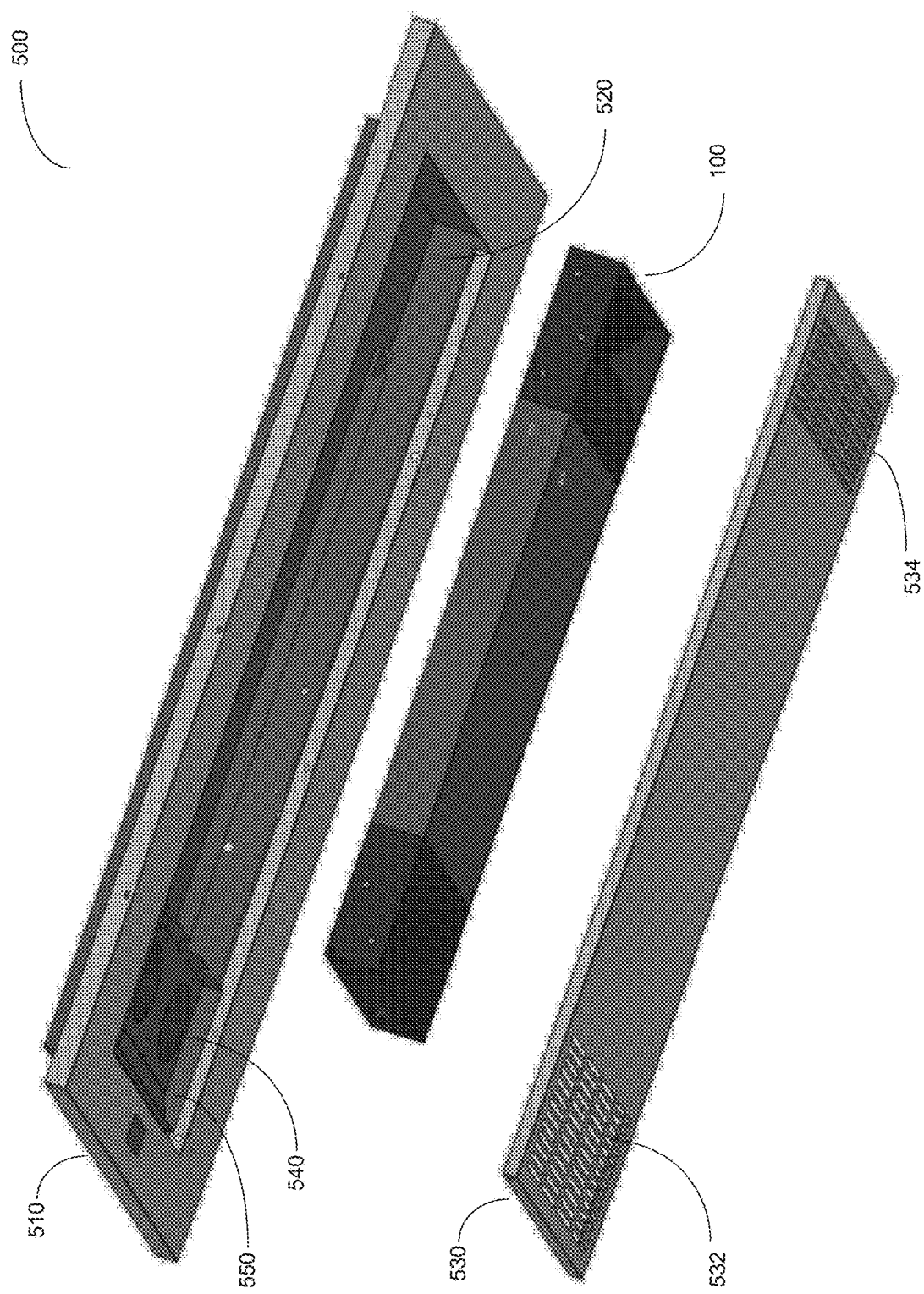
FIG. 5 shows an exploded view of an example air purification system implemented in accordance with aspects of the present disclosure.

FIG. 5 schematically illustrates an exploded view of an example air purification system implemented in accordance with aspects of the present disclosure. As shown in FIG. 5, the example air purification system 500 includes a housing 510 containing an opening 520 configured to receive the removable UV lamp cartridge 100. The housing 510 have a form factor of a convex polyhedron formed by flat panel facets, the bottom facets of the polyhedron is removed and effectively replaced by the lid 530, which may be removed to provide access for replacing the UV lamp cartridge 100.

In some implementations, at least part of the surface of the lid 530 is occupied by a group of suction louvers collectively forming an air inlet 532, while another part of the surface of the lid 530 is occupied by a group of exhaust louvers collectively forming an air outlet 534.

In the illustrative example of FIG. 5, the air is drawn at a pre-defined (e.g., 45 degrees) angle with respect to the imaginary longitudinal axis of the housing 510 through the air inlet 532 and, after passing through the UV lamp cartridge 100, discharged at another pre-defined (e.g., 45 degrees) angle with respect to the imaginary longitudinal axis of the housing 510 through air outlet 534. The air intake and discharge parameters are defined by the shapes, positions, configurations (e.g., the angle of the slats forming the louvers), and/or sizes of the air inlet 532, the air outlet 534, and/or the louvers forming the air inlet 532 and the air outlet 534. The shapes, positions, configurations, and/or sizes of the air inlet 532, the air outlet 534, and/or the louvers forming the air inlet 532 and the air outlet 534 may be adjusted in order to accommodate a specific application and/or provide the desired performance parameters (i.e., the volume of the air passing through the louvers in a unit of time, the noise levels, etc.).

In some implementations, a particle absorbing filter (not shown in FIG. 5) may be positioned adjacently to the air inlet 532 and is employed for absorbing the particles that are contained in the air passing through the filter. The particle absorbing filter may be represented, e.g., by a high-efficiency particulate absorbing (HEPA) filter. The type, size, and/or other parameters of the particle absorbing filter may be chosen to satisfy the requirements of a particular application. In particular, the size of the particle absorbing filter may be chosen that is capable to provide a requisite performance measured by the volume of the air processed by the air purification system 500 in a unit of time.

The housing 510 may also contain a fan 540 and an air conduit 550 shaped to efficiently drive the air from the air inlet 532 to the fan 540 and then to the air inlet 120 of the UV lamp cartridge 100. In some implementations, the fan 540 may be driven by a direct current (DC) motor, and its rotation rate may be controlled by a pulse width modulator (PWM) driver.

In various implementations, the above-referenced and/or other parts of the air purification system may be made of metal, plastic, composite, and/or other suitable materials. Surfaces of the above-referenced parts may be machined, polished, coated, painted, and/or otherwise processed.

The housing may further contain a receptacle (not shown in FIG. 5) for the self-aligning connector of the replaceable UV lamp cartridge 100, to make electrical contact once the UV lamp cartridge 100 in inserted into the air purification system 500, in order to supply the voltage to the UV radiation emitting devices 150.

The housing may further contain a control circuit (not shown in FIG. 5) for controlling the operation of fan 540 and the UV radiation emitting devices 150 of the UV lamp cartridge 100. In some implementations, the control circuit may enable additional functionalities such motion detection and/or Internet-of-Things (IOT) capabilities. In an illustrative example, one or more motion detectors disposed within and/or outside of the air purification system 100 may transmit motion detection signals to the control circuit, which may switch the radiation emitting devices 150 an the fan 540 on responsive to receiving motion detection signal(s) from one or more motion detectors, and may further switch the radiation emitting devices 150 and the fan 550 of upon expiration of a timeout triggered by the motion detection signal(s). In another illustrative example, the control circuit may, in the absence of motion detector signals, maintain the speed of the fan 550 and/or voltage level supplied to the UV radiation emitting devices 150 at their respective standby levels. Upon receiving motion detection signal(s) from one or more motion detectors, the control circuit may increase the speed of the fan 550 and/or voltage level supplied to the UV radiation emitting devices 150, and may return to the standby fan speed and radiation emitting device voltage levels upon expiration of a timeout triggered by the motion detection signal(s). In yet another illustrative example, the control circuit 106 may receive control signals (e.g., fan on/off, UV radiation emitting devices on/off, fan speed, voltage level supplied to the UV radiation emitting devices 150, etc.) via a wireless communication interface (e.g., Bluetooth or Wi-Fi interface).

Accordingly, a field-replaceable ultraviolet (UV) lamp cartridge implemented in accordance with aspects of the present disclosure may include a tamper-proof UV energy absorbing shell containing one or more UV radiation emitting devices, an air inlet disposed at a first end of the tamper-proof UV energy absorbing shell, an air outlet disposed at a second end of the tamper-proof UV energy absorbing shell, and a self-aligning connector for receiving external voltage to be supplied to the UV energy emitting devices.

In some implementations, the tamper-proof UV energy absorbing shell may be formed by a plurality of panels arranged to form a convex polyhedron.

In some implementations, the tamper-proof UV energy absorbing shell may be configured to absorb UV radiation emitted by the UV radiation emitting devices, such that intensity of total UV radiation emitted by the UV lamp cartridge would not exceed a predefined threshold intensity value (e.g., 0.1 micro-Watts per square centimeter of a recipient surface).

In some implementations, the tamper-proof UV energy absorbing shell contains a plurality of reflective surfaces collectively forming a light path to be followed by UV energy emitted by the UV radiation emitting devices.

In some implementations, the tamper-proof UV energy absorbing shell contains a plurality of low reflectance surfaces, such that each reflectance surface is configured to absorb at least a pre-defined portion of UV energy that is incident upon the reflective surface.

In some implementations, the tamper-proof UV energy absorbing shell contains one or more air trims that are configured to control a flow of air moving through the tamper-proof UV energy absorbing shell.

In some implementations, the tamper-proof UV energy absorbing shell contains a plurality of shapes that are configured to absorb at least a pre-defined portion of UV energy emitted by the UV radiation emitting devices and to control a flow of air moving through the tamper-proof UV energy absorbing shell.

Furthermore, an air purification system, device, or apparatus ("air purification system") implemented in accordance with aspects of the present disclosure, may include a housing and a removable ultraviolet (UV) lamp cartridge detachably attached to the housing. The removable UV lamp cartridge may include a tamper-proof UV energy absorbing shell containing one or more UV radiation emitting devices, an air inlet disposed at a first end of the tamper-proof UV energy absorbing shell, and an air outlet disposed at a second end of the tamper-proof UV energy absorbing shell.

In some implementations, air purification system further includes a fan disposed within the housing.

In some implementations, air purification system further includes a particle absorbing filter disposed within the housing.

In some implementations, air purification system further includes a safety switch configured to cut a power supply to the UV radiation emitting devices responsive to determining that a lid of the housing has been opened.

In some implementations, air purification system further includes a safety switch configured to cut a power supply to the UV radiation emitting devices responsive to determining that integrity of the housing has been compromised.

In some implementations, the tamper-proof UV energy absorbing shell may be configured to absorb UV radiation emitted by the UV radiation emitting devices, such that intensity of total UV radiation emitted by the UV lamp cartridge would not exceed a predefined threshold intensity value.

In some implementations, the tamper-proof UV energy absorbing shell contains a plurality of reflective surfaces collectively forming a light path to be followed by UV energy emitted by the UV radiation emitting devices.

In some implementations, the tamper-proof UV energy absorbing shell contains a plurality of low reflectance surfaces, such that each reflectance surface is configured to absorb at least a pre-defined portion of UV energy that is incident upon the reflective surface.

In some implementations, the tamper-proof UV energy absorbing shell contains one or more air trims that are configured to control a flow of air moving through the tamper-proof UV energy absorbing shell.

In some implementations, the tamper-proof UV energy absorbing shell contains a plurality of shapes that are configured to absorb at least a pre-defined portion of UV energy emitted by the UV radiation emitting devices and to control a flow of air moving through the tamper-proof UV energy absorbing shell.

In some implementations, the replaceable UV lamp cartridge further comprises a self-aligning connector for receiving external voltage to be supplied to the UV energy emitting devices. The self-aligning connector may further ensure a pre-defined position and orientation of the replaceable UV lamp cartridge within the housing of the air purification system.

What is claimed is:

1. An air purification system, comprising:
   a housing;
   a removable ultraviolet (UV) lamp cartridge detachably attached to the housing, wherein the removable UV lamp cartridge comprises a tamper-proof UV energy absorbing shell containing one or more UV radiation emitting devices, an air inlet disposed at a first end of the tamper-proof UV energy absorbing shell, and an air outlet disposed at a second end of the tamper-proof UV energy absorbing shell; and
   a safety switch configured to cut a power supply to the UV radiation emitting devices responsive to determining that a lid of the housing has been opened.

2. The air purification system of claim 1, further comprising:
   a fan disposed within the housing.

3. The air purification system of claim 1, further comprising:
   a particle absorbing filter disposed within the housing.

4. The air purification system of claim 1, wherein the tamper-proof UV energy absorbing shell is configured to absorb UV radiation emitted by the UV radiation emitting devices, such that intensity of total UV radiation emitted by the UV lamp cartridge does not exceed a predefined threshold intensity value.

5. The air purification system of claim 1, wherein the tamper-proof UV energy absorbing shell contains a plurality of reflective surfaces collectively forming a light path to be followed by UV energy emitted by the UV radiation emitting devices.

6. The air purification system of claim 1, wherein the tamper-proof UV energy absorbing shell contains a plurality of low reflectance surfaces, wherein each low reflectance surface is configured to absorb at least a pre-defined portion of UV energy that is incident upon the low reflectance surface.

7. The air purification system of claim 1, wherein the tamper-proof UV energy absorbing shell contains one or more air trims that are configured to control a flow of air moving through the tamper-proof UV energy absorbing shell.

8. The air purification system of claim 1, wherein the tamper-proof UV energy absorbing shell contains a plurality of shapes that are configured to absorb at least a pre defined portion of UV energy emitted by the UV radiation emitting devices and to control a flow of air moving through the tamper-proof UV energy absorbing shell.

9. The air purification system of claim 1, wherein the removable UV lamp cartridge further comprises a self-aligning connector for receiving external voltage to be supplied to the UV radiation emitting devices.

10. The air purification system of claim 9, wherein the self-aligning connector ensures a pre-defined position and orientation of the removable UV lamp cartridge within the housing of the air purification system.

11. An air purification system, comprising:
a housing;
a removable ultraviolet (UV) lamp cartridge detachably attached to the housing, wherein the removable UV lamp cartridge comprises a tamper-proof UV energy absorbing shell containing one or more UV radiation emitting devices, an air inlet disposed at a first end of the tamper-proof UV energy absorbing shell, and an air outlet disposed at a second end of the tamper-proof UV energy absorbing shell; and
a safety switch configured to cut a power supply to the UV radiation emitting devices responsive to determining that integrity of the housing has been compromised.

12. The air purification system of claim 11, further comprising:
a fan disposed within the housing.

13. The air purification system of claim 11, further comprising:
a particle absorbing filter disposed within the housing.

14. The air purification system of claim 11, wherein the tamper-proof UV energy absorbing shell is configured to absorb UV radiation emitted by the UV radiation emitting devices, such that intensity of total UV radiation emitted by the UV lamp cartridge does not exceed a predefined threshold intensity value.

15. The air purification system of claim 11, wherein the tamper-proof UV energy absorbing shell contains a plurality of reflective surfaces collectively forming a light path to be followed by UV energy emitted by the UV radiation emitting devices.

16. The air purification system of claim 11, wherein the tamper-proof UV energy absorbing shell contains a plurality of low reflectance surfaces, wherein each low reflectance surface is configured to absorb at least a pre-defined portion of UV energy that is incident upon the low reflectance surface.

17. The air purification system of claim 11, wherein the tamper-proof UV energy absorbing shell contains one or more air trims that are configured to control a flow of air moving through the tamper-proof UV energy absorbing shell.

18. The air purification system of claim 11, wherein the tamper-proof UV energy absorbing shell contains a plurality of shapes that are configured to absorb at least a pre defined portion of UV energy emitted by the UV radiation emitting devices and to control a flow of air moving through the tamper-proof UV energy absorbing shell.

19. The air purification system of claim 11, wherein the removable UV lamp cartridge further comprises a self-aligning connector for receiving external voltage to be supplied to the UV energy emitting devices.

20. The air purification system of claim 19, wherein the self-aligning connector ensures a pre-defined position and orientation of the removable UV lamp cartridge within the housing of the air purification system.

* * * * *